United States Patent
Alexandre et al.

(10) Patent No.: US 7,404,808 B2
(45) Date of Patent: Jul. 29, 2008

(54) NEEDLELESS SYRINGE COMPRISING AN OPTIMIZED INJECTOR-RECEPTACLE

(75) Inventors: Patrick Alexandre, Gray (FR); Georges Baud, La Crau (FR); Bernard Brouquieres, Toulon (FR)

(73) Assignee: Crossject, Paris (FR)

( * ) Notice: Subject to any disclaimer, the term of this patent is extended or adjusted under 35 U.S.C. 154(b) by 47 days.

(21) Appl. No.: 10/546,251

(22) PCT Filed: Apr. 9, 2004

(86) PCT No.: PCT/FR2004/000881

§ 371 (c)(1),
(2), (4) Date: Aug. 19, 2005

(87) PCT Pub. No.: WO2004/093944

PCT Pub. Date: Nov. 4, 2004

(65) Prior Publication Data
US 2007/0167906 A1    Jul. 19, 2007

(51) Int. Cl.
*A61M 5/30*    (2006.01)
(52) U.S. Cl. .................................... 604/69; 604/68
(58) Field of Classification Search ... 604/68; *A61M 5/30*
See application file for complete search history.

(56) References Cited
U.S. PATENT DOCUMENTS
4,668,223 A    5/1987    Grotenhuis 2002/0156418 A1 * 10/2002 Gonnelli et al. ............... 604/69
2003/0050596 A1 *  3/2003 Alexandre et al. ............ 604/69

FOREIGN PATENT DOCUMENTS

| | | |
|---|---|---|
| EP | 0 896 827 A1 | 2/1999 |
| WO | WO 00/48654 A1 | 8/2000 |
| WO | WO 01/58512 A1 | 8/2001 |
| WO | WO 158512 A1 * | 8/2001 |

* cited by examiner

*Primary Examiner*—Nicholas D. Lucchesi
*Assistant Examiner*—Laura A Bouchelle
(74) *Attorney, Agent, or Firm*—Oliff & Berridge, PLC

(57) ABSTRACT

The invention relates to the realm of needleless syringes used for injecting liquid active substances. Said syringe comprises a reservoir that is enclosed by means of displaceable plugs which trap the liquid. The reservoir is initially isolated from an injector-receptacle (37) which is provided with at least two peripheral injection conduits (38) that are arranged outside the receptacle (37). Said receptacle (37) encompasses a pocket bore (31) which accommodates the plug located downstream such that the optimized inlets (39) of the conduits are unobstructed. The face of the receptacle (37), which is located upstream, comprises a multilobed sealing joint (34) which is disposed parallel to and as close as possible to the edges of the bore (31) and the inlets (39). The aim of the invention is to create an injector-receptacle (37) that is optimized regarding discharging and the resistance thereof to the injection pressure.

19 Claims, 2 Drawing Sheets

NEEDLELESS SYRINGE COMPRISING AN OPTIMIZED INJECTOR-RECEPTACLE

The present invention falls within the field of disposable needleless syringes; such syringes are used for intradermal, subcutaneous and intramuscular injections of liquid active principle for therapeutic use in human or veterinary medicine.

A first requirement of such needless syringes is that of long-term compatibility between the liquid active principle and the reservoir which contains it. Another requirement is to have a reservoir that is transparent so that the correct filling of the reservoir can be checked before the syringe is used. These requirements lead to the production of essentially transparent reservoirs made of a material compatible with the active principle for the desired length of time: this is generally borosilicate glass for pharmaceutical use: glass of type I or II.

The initial phase of the injection is critical to the penetration into the skin of the jet or jets of liquid, depending on whether the syringe has one or several injection ducts. The latter configuration being favorable to reducing the discomfort. The final bioavailability depends on this initial phase being performed correctly; it assumes that the liquid in the injection ducts is quickly brought up to speed without multiple jerkiness in the jets when the water hammer effect is too great for this rapid acceleration.

Patent application WO 01/58512 describes a needleless syringe comprising a reservoir closed by movable upstream and downstream plugs entrapping a liquid active principle; said reservoir is initially isolated from an injector or receptacle which comprises at least two injection ducts situated on its outer lateral face and a blind central bore in which the downstream plug becomes housed in such a way as to uncover the inlets to the injection ducts as the downstream stopper/active principle/upstream stopper assembly is moved through the action of a driving device in order to perform the injection.

A first difficulty with this syringe is that the inlets to the injection ducts are not optimized. They are not optimized, on the one hand, with respect to pressure drops and, on the other hand, with respect to residual liquid losses in the dead volumes. In that application, the inlets are radial grooves over the entire upstream face of the receptacle. Finally, the shape of the upstream opening of the central bore is not optimized and may tear the downstream stopper when the latter engages therein.

An important problem is not satisfactorily solved in that invention, and that is the problem of minimizing the pressure forces on the receptacle during the injection phase in the knowledge that these forces are of decisive importance to the receptacle. Given the configuration produced, the entire surface of the receptacle bearing against the reservoir is subjected to the pressure because the sealing is transferred off toward the binding material on the outside of the reservoir because the use of an O-ring seal is impossible here particularly because of the radial inlet grooves to the injection ducts.

The present invention sets out to solve the problems of optimizing the inlets to the injection ducts and above all those of reducing the pressure forces on the receptacle during the injection phase.

The present invention relates to a needleless syringe comprising a body housing a cylindrical reservoir closed by a movable upstream stopper and a movable downstream stopper entrapping an active principle and comprising, downstream, an injector-receptacle termed more briefly receptacle with at least two peripheral injection ducts, said receptacle bearing against the reservoir and comprising a blind bore the free height of which allows the inlets to the peripheral ducts to be uncovered when the downstream stopper is brought into contact with the closed end of the bore of said receptacle through the operation of a driving means moving the upstream stopper/liquid/downstream stopper assembly, and said syringe is characterized in that each inlet comprises a spot face positioned on the injection duct and is connected to a radial channel opening into the central bore. As a preference, said spot face is centered on the injection duct.

In this application, the qualifier "downstream" is used to denote any component close to the injection site or any part of a component facing toward this injection site; this site is the patient's skin. By contrast, the qualifier "upstream" will be used for any component distant from the injection site or any part of a component facing away from this site. Thus, the receptacle comprises a downstream face facing toward the patient's skin and an upstream face which is opposite it and bears against the reservoir; these downstream and upstream faces are connected by a lateral face.

For this invention, a liquid active principle or drug is essentially intended to mean a liquid of some viscosity, or a mixture of liquids, or a gel. The active principle may be a solid dissolved in a solvent suited to injection. The active principle may be a solid in pulverulent form placed in suspension, of greater or lesser concentration, in an appropriate liquid. The particle size of the solid active principle and the shape of the duct need to be tailored to avoid blockages.

The reservoir, which is essentially cylindrical, is made of type I or type II glass; however, it may be made of any other material that is transparent and compatible with the active principle. The upstream and downstream faces are essentially flat, the planes containing them being perpendicular to the axis of symmetry of the reservoir. The upstream and downstream faces bear respectively on the body of the syringe and the receptacle. The bearing faces of these two components have seals the characteristics of which will be specified later on.

An injection duct crosses the entire height of the receptacle from the upstream face to the downstream face. The injection ducts, because there are at least two of these, are said to be peripheral because they are arranged in the receptacle around the blind central bore. They communicate with said central bore only via inlets described hereinafter. The injection duct has a cross section that may vary from upstream to downstream on the one hand for reasons associated with its production and on the other hand in order to obtain a jet that is fine and rapid enough to penetrate the patient's skin to the desired depth. In general, the injection ducts are identical, uniformly distributed about the blind central bore and have axes parallel to the axis of the receptacle, but they may also be different.

The driving means which will act on the upstream stopper may be a mechanical motor: expansion of a compressed spring, or a spring of the pneumatic type: expansion of a compressed gas, or a pyrotechnic gas: expansion of a combustion gas.

The way in which the syringe works is as follows: the driving means will act on the upstream stopper and move the upstream stopper/liquid/downstream stopper assembly because the liquid is incompressible. The downstream stopper moves and becomes housed in the blind bore of the receptacle until it comes into contact with the closed end of said bore. The height of this bore is such that, when the downstream stopper is in contact with the closed end of said bore, the inlets to the injection ducts, on the periphery of the bore of the receptacle, are uncovered; the liquid is discharged into them and is injected by the movement of the upstream stopper which continues until the reservoir is emptied: the upstream stopper is then in contact with the downstream stopper.

The inlet to an injection duct, which inlet is situated on the upstream face of the receptacle, comprises a spot face positioned and preferably centered on the injection duct and a radial channel connecting said spot face to the blind central bore of said receptacle.

The spot face forming the inlet to the injection duct has a diameter ranging between about 1.1 times and about 1.5 times the diameter of the injection duct, and preferably about 1.2 times this diameter. The diameter of the duct taken here for reference is the diameter near the upstream face of the receptacle. The depth of the spot face ranges between about 0.5 times and about 0.7 times the diameter of the injection duct and is preferably about 0.6 times this diameter.

A radial channel, connecting to the aforementioned spot face, connects the bore to the injection duct. The depth of said radial channel is equal to that of the spot face. The width of this radial channel is either constant and equal to the diameter of the spot face or this width increases from the width it has where it meets the spot face to a higher value where it opens into the central bore: this higher value will, however, remain smaller than about 1.4 times the diameter of the injection duct.

The spot face may be understood in its customary technical sense: that is to say as a machined feature in the form of an upright circular recess made around a hole, in which case the lateral face of the spot face is perpendicular to the flat upstream face of the receptacle and to the closed end of the spot face.

However, a spot face may also be understood in a broader sense in which the lateral face of the recess is no longer perpendicular but oblique with respect to the upstream face and even meets the closed end of the recess in the form of a rounded corner. In this case, the dimensions of the spot face and of the radial channel will be measured at their upstream part.

The upstream face of the receptacle comprises a central orifice consisting of the blind central bore and the inlets connecting said bore to the injection ducts. The edges of this orifice are the intersections of the flat upstream face and of the lateral faces of the bore and of the inlets. Theoretically, these edges correspond to fairly sharp edges, but these edges are blunted with an appropriate radius of curvature especially on the portions which are the edges of the central bore and those of the intersection of the radial channels so as not to damage or tear the downstream stopper when it engages in the central bore at the start of operation and passes "over" these portions.

This upstream face comprises a multilobed seal parallel and as close as possible to the edges of this central orifice. The seal is said to be parallel to the edges because its distance to the edge, evaluated in a direction perpendicular to the edge, is constant, the seal is said to be as close as possible to the edge because this distance is as short as possible given the ways in which the receptacle is formed. The seal is multilobed because it surrounds on the outside the inlets to the injection ducts while being parallel and as close as possible to the edge; in this instance, the idea of on the outside being evaluated in terms of remoteness from the axis.

By comparison with a circular seal surrounding the bore and the inlets to the ducts, the multilobed seal as defined reduces the surface area of the receptacle that is exposed to the pressure of the liquid during the injection phase because, in the case of the sectors between the ducts, the multilobed seal is closer to the edge of the bore than a circular seal.

According to a first embodiment, the multilobed seal is an added seal, housed in a groove of mating shape made on the upstream face of the receptacle. This embodiment entails fitting the seal in the groove using precise methods then precise handling operations to mount it bearing against the reservoir, then in the body of the syringe.

According to a preferred second embodiment, when the receptacle is produced by injection molding, the multilobed seal as previously described is produced by two-shot injection molding. The multilobed and two-shot injection molded seal has a central additional thickness on its exterior face; the compression and deformation of this additional thickness as the receptacle and the reservoir are pushed together ensures sealing.

The two-shot injection molding technique, known from elsewhere, consists, when the main component, in this case the receptacle, has been injected and has not yet hardened, in taking it up again and, using an appropriate mold, injecting the material that will produce the multilobed seal into the cavity provided for this purpose in the receptacle. This cavity must of course be parallel to the edges of the orifice and as close as possible to the edge. This technique can be likened to the technique of overmolding the multilobed seal.

The two-shot injection molded multilobed seal has the advantages of yielding, almost directly after this second injection, a single receptacle/seal component so that the assembly of the syringe then continues.

Advantageously, the central bore of the receptacle is of essentially frustoconical shape, the inlet diameter of said bore being equal to the inside diameter of the reservoir and the smallest diameter of the bore being toward the closed end of said bore, a running generatrix of the lateral part making an angle of between about 2° and about 9° with the axis of symmetry of the bore and this angle is preferably about 7°. The closed end of the bore connects to the lateral part with an appropriate rounding.

The depth of the bore is such that, when the downstream stopper is bearing against the closed end of the bore, the inlets to the injection ducts are uncovered and place the reservoir in communication with the injection ducts. The relatively open shape of the bore means that the downstream stopper enters this cavity and deforms uniformly during this phase, thus deadening the shock and limiting the forces on the receptacle during this phase of the operation.

The present invention applied to a prefilled one-use syringe has the advantage of allowing a separation to be made, within the device, between two parts. One part which will be termed the pharmaceutical part comprising the body and the reservoir with the movable upstream and downstream stoppers and possibly the injector/receptacle: this subassembly may be processed under the conditions of the pharmaceutical industry, particularly in terms of sterilization and asepsis.

This subassembly will be integrated into the remainder of the syringe, the elements of which have been assembled elsewhere, this assembly being performed under conditions which are not as strict as those associated with the pharmaceutical industry.

When the downstream stopper is housed in the bore of the receptacle, the syringe becomes very difficult to reuse. This arrangement therefore also has the advantage of preventing said syringe from being reused for purposes other than the initial therapeutic use.

Finally, this configuration has the advantage of avoiding any possible leaks of liquid through the injection ducts before the injection is administered. What happens is that the device is frequently agitated, this even sometimes being recommended in order to examine the clarity of the liquid or in order to homogenize the mixture when the liquid contains particles in suspension. The fact that the active principle is isolated, prior to injection, from the ducts affords ultimate protection against this risk of loss.

The invention is set out in detail hereinbelow with the aid of figures depicting various particular embodiments of the invention.

Figure 5:
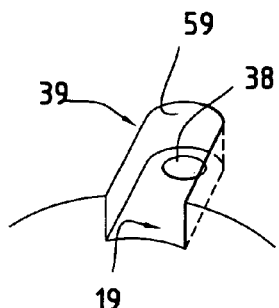
Figure 6:
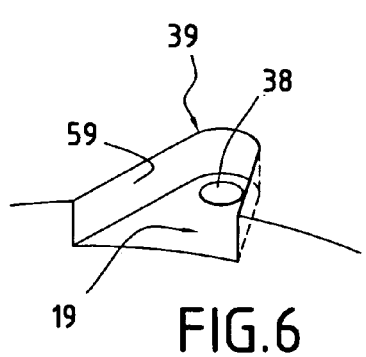
Figure 7:
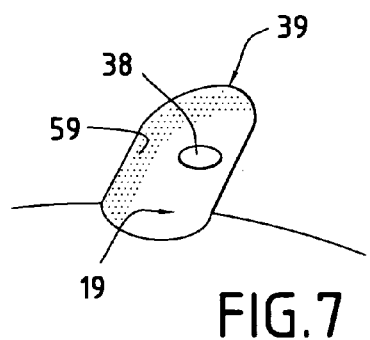

FIGS. 5, 6 and 7 schematically and in perspective depict various shapes of inlets to the injection ducts.

Figure 1:
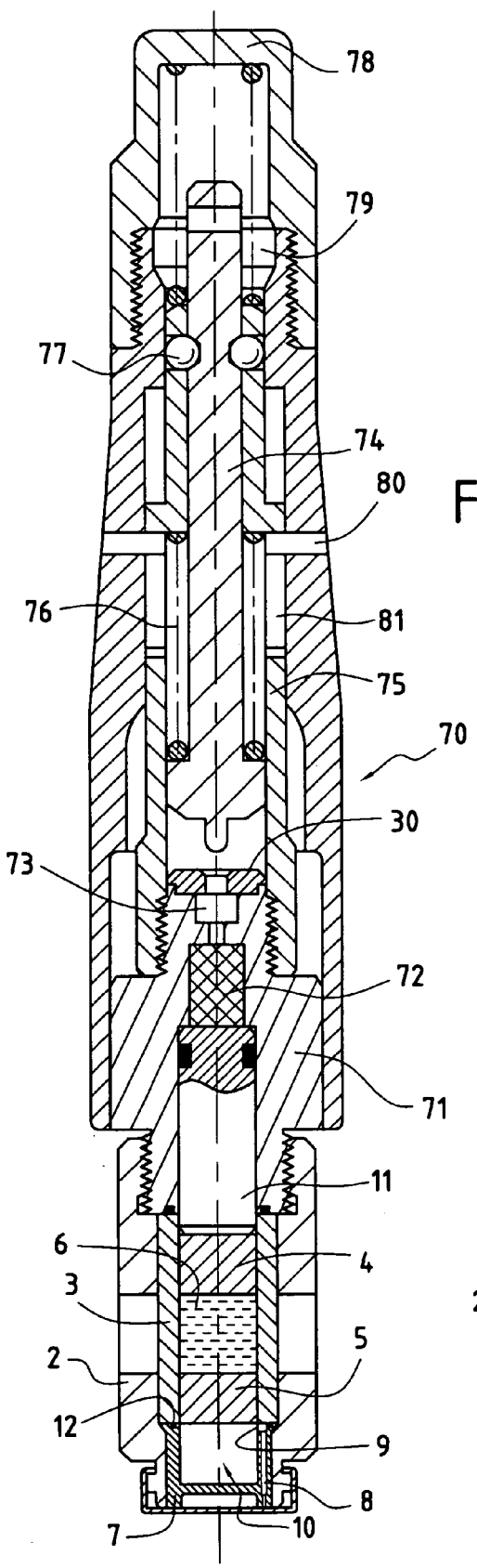
FIG. 1 depicts a longitudinal section through a syringe according to a first embodiment of the invention.

FIG. 1 depicts, in partial longitudinal section, a syringe according to the invention; it is depicted vertically, the injection system pointing downward which will be the downstream direction.

The syringe 1 comprises a body 2 in which there is housed a reservoir 3 containing the liquid active principle 6. Placed at the downstream end of the body 2 is a receptacle 7 comprising, for example, three injection ducts such as the duct 8. The injection system is covered with external protection to ensure the asepsis of the syringe: this protection comprises an elastomer membrane pressed against the exterior face of the injector by a fine metal disk crimped around this end of the syringe. This protection will be removed before injection. At its opposite end, the body 2 of the syringe is fixed to a driving means 70 which, in this example, is a pyrotechnic gas generator; this will be described later on. The reservoir 3 presses against the body 71 of the driver 70, sealing being afforded by a circular O-ring seal.

The body 2 of the syringe comprises two diametrically opposed apertures for viewing the active principle contained in the reservoir 3: these are simply two oblong openings in the body. At the downstream end of the body 2 of the syringe there is push fitted, into a bore of appropriate shape, a cylindro-conical receptacle 7 which will be described hereinafter. Pressing against this receptacle 7 and centered in the downstream end of the body 2 there is a glass reservoir 3; this reservoir is a tube. Upstream, the body 2 of the syringe accepts the body 71 of the driving means which is centered around the other end of the reservoir. The reservoir 3 is essentially a tube closed at both ends by movable upstream 4 and downstream 5 stoppers; these stoppers are preferably piston plungers customarily used in syringes: these are components obtained by the molding of elastomers that have long-term compatibility with the active principle: each component incorporates the piston and sealing functions through the producing of bulges or lips (not detailed in the figures). The elastomers customarily used for manufacturing these components are, for example, chlorobutyls or bromobutyls, the Shore hardness of which is set between about 45 and about 70. These components may receive surface treatments particularly to make them easier to move in the tubular reservoir. In the free state, the piston plunger has a diameter about 10 percent greater than the inside diameter of the tube that will accommodate it, and the height of the piston plunger is about 0.5 to 0.8 times this diameter. When the piston plunger is engaged in the tube, because of the deformations, its height is equal to about 0.6 times to about 1.0 times the inside diameter of the reservoir.

In this example, the receptacle 7 is a component of cylindro-conical exterior shape which comprises a central bore 10 in which the downstream stopper 5 will be accommodated. On its periphery, the receptacle has three injection ducts just one of which, identified as 8, is visible in this section. The diameter of the bore is equal to that of the reservoir. The free height of the blind bore 10 of the receptacle 7 is equal to that of the downstream stopper 5 mounted in the reservoir 3. When the downstream stopper 5 has reached the closed end 7a of the receptacle, the inlet 9 (on the reservoir 3 side) of the injection ducts 8 is placed in communication with the liquid 6; the liquid flows at a speed corresponding to the pressure transmitted by the upstream stopper 4.

In this embodiment, the driving means acts on the upstream stopper by way of a piston 11 the effective cross section of which is equal to that of the upstream stopper 4. This piston 11 is in contact with the upstream stopper 4 and there is therefore no shock or hammer effect at the beginning of operation. This piston 11 by virtue of its sealing system prevents the gases produced by the combustion of the charge 72 from coming into contact with the upstream stopper and therefore prevents any possible damage to the latter or leakage of gas toward the active principle contained in the reservoir. This piston 11, of a suitable color, may also serve as an indicator of operation by being visible in the viewing apertures in the body 2 of the syringe.

We shall now describe the main elements of the pyrotechnic generator 70. It comprises, in the body 71 above the piston, a pyrotechnic charge 72 the combustion of which is initiated by a primer 73 impacted by a striker 74. The primer 73 is housed in a primer holder. In the initial position, the striker 74 is held, in the striker guide 75, securely screw-fastened to the body 71, by at least one ball, such as the ball 77, partially engaged in a groove in the striker. The percussion device comprises a push button 78 with a groove 79 and an internal spring 76.

The push button 78 slides over the outside of the striker guide 75 and is held in place by pins 80 running in lateral slots 81. This push button 78 here is the triggering member.

Of course, in order to initiate combustion of the pyrotechnic charge 72, without departing from the scope of the invention, it is possible to use initiation devices other than the device involving a striker described here. Without wishing to be exhaustive, we mention by way of example initiation devices involving an electric battery, or piezoelectrically initiated devices.

The pyrotechnic gas generator could be replaced by a gas generator consisting of a reservoir of compressed gas closed by a rapidly opening valve. The triggering member will open said valve, the compressed gases in the reservoir will expand and act on the pushing means.

For use, having removed the asepsis cap, and placed the downstream face of the injector onto the skin of the subject to be treated, the operator using his or her thumb presses the push button 78 which depresses, compressing the spring 78. The push button moves until the groove 79 comes level with the groove of the striker 74, the balls, such as the ball 77, that hold the striker 74, move aside into the groove 79 and release the striker which will violently strike the primer 73, initiation of which ignites the pyrotechnic charge 72. The striker 74 bearing against the primer holder 30 holds the primer in place and ensures sealing: the combustion gases do not travel back toward the push button.

The combustion of the pyrotechnic charge will produce gases which act on the piston 11.

FIG. 1 depicts a syringe according to the invention, in the form of a pen: all the elements have the same central axis but are superposed. Without departing from the scope of the present invention, other arrangements are conceivable, for example the driving part may be at a certain angle to the reservoir/receptacle part in order to achieve more compact shapes like the one described for example in patent application FR 2 815 544.

Figure 2:
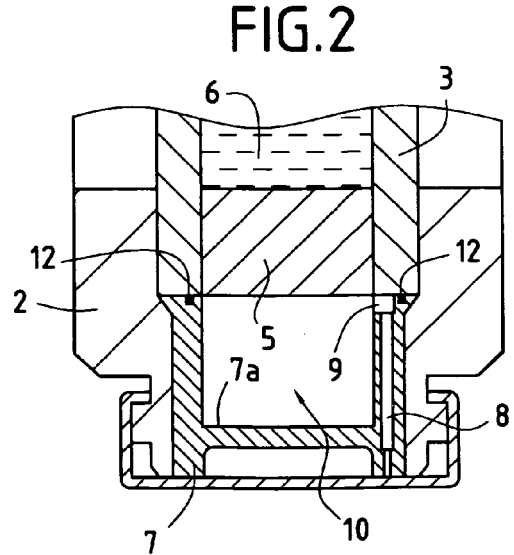
FIG. 2 is an enlargement of the downstream part of said syringe.

FIG. 2 is an enlargement of the downstream part of the syringe already described.

The receptacle 7 is a component of cylindro conical exterior shape push fitted into the body 2 of the syringe.

The blind central bore 10 is essentially cylindrical. As a preference, the upstream edge, meeting the upstream face of the receptacle and the bore, comprises a rounded portion with enough of a radius of curvature that the downstream stopper is not torn when it enters the bore at the start of operation.

The receptacle comprises several injection ducts of which just one, identified as 8, is visible in this view. An inlet 9 connects the bore, more precisely the upstream part of said bore, to the injection duct. When the downstream stopper is entirely housed in the bore, liquid, which comes to occupy the upstream part, can flow as far as the injection duct.

It is possible to see a sectioned view of a multilobed seal 12 placed in a seal groove which is as close as possible to the edges of the bore and surrounds the spot face. This aspect will be described in greater detail hereinafter.

Figure 3:
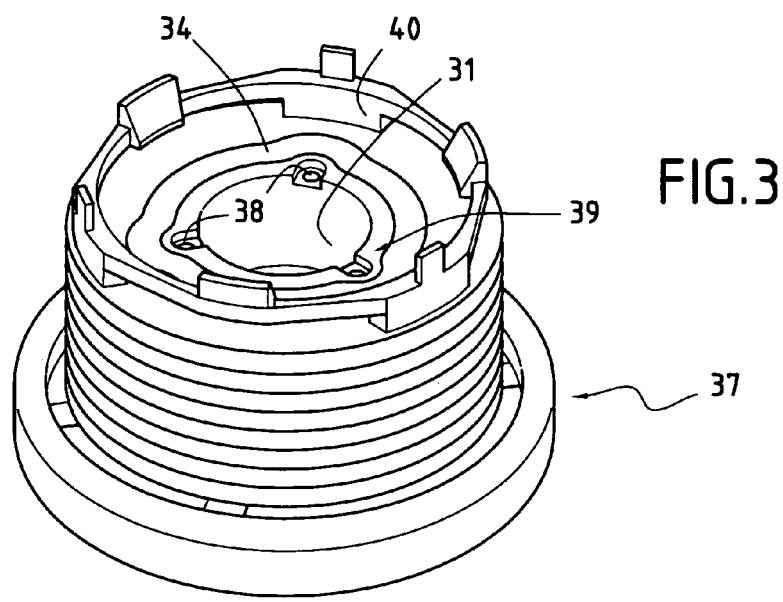
FIG. 3 is a perspective view of another exemplary embodiment of the receptacle according to the invention.
Figure 4:
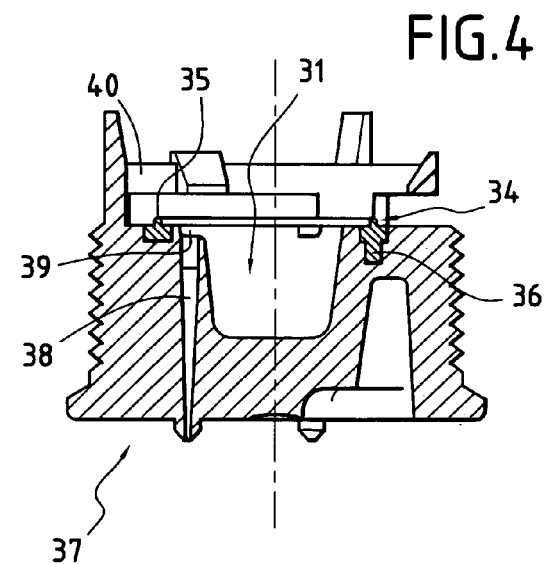
FIG. 4 depicts a section through said receptacle on a plane passing through the central axis of the receptacle and containing the axis of an injection duct.

FIGS. 3 and 4 depict another embodiment of a receptacle of a syringe according to the invention. In this example, the receptacle is obtained by injection molding a polycarbonate compatible with the envisioned use.

Said receptacle 37 comprises, on its lateral face, a lateral screw thread for screw fastening into a body of appropriate shape. The receptacle comprises three peripheral injection ducts, of which just one, 38, is visible in the sectioned view. The three injection ducts are, in this example, identical and uniformly distributed about the central bore 31 of the receptacle; they are connected to said bore by inlets 39. Given the method of manufacture, by injection molding, of the receptacle, the upstream part of the duct is fairly wide, about 0.8 mm in diameter over about 4 mm to about 5 mm in height, this portion is cylindrical or cylindroconical; it is extended in the downstream direction by a narrower part with a diameter of about 0.1 mm and about 2 mm to about 3 mm high, to produce the jet which will penetrate the patient's skin to a greater or lesser depth.

In this embodiment, the upstream face of the receptacle comprises a clipping device 40 which will accept and hold a reservoir comprising bulges at its ends; said reservoir may be prefilled before it is mounted on the receptacle; this stand alone assembly in this example constitutes the pharmaceutical part of the syringe; it may be handled as an independent entity. This device is described in greater detail elsewhere.

The upstream face of the receptacle comprises a three-lobed seal 34 because there are three injection ducts in this example. This seal is manufactured by two-shot injection molding. The three-lobed seal is parallel and as close as possible to the edges of the bore and to the edges of the inlets in the sense that we have defined earlier.

The sectioned view shows that the cavity accepting the three-lobed seal is of rectangular section. The three-lobed seal occupies this entire cavity with an additional thickness 35 in the central part of its free upstream face because the reservoir has not yet been mounted on the receptacle.

In order to anchor the three-lobed seal more firmly in the cavity of the receptacle, the downstream face of the seal has uniformly distributed anchoring pegs which become housed in orifices prepared in the cavity at the time of the injection-molding of the receptacle. Such a peg 36 can be seen on the opposite side to the injection duct.

The elastomer chosen for the two-shot injection molding of the seal must adhere appropriately to its support; this is one of the benefits of the two-shot injection molding technique; it must also be capable of long endurance and its hardness must be sufficient to fulfill the sealing function. A Shore hardness of about 75 is suitable for this application. When the receptacle is made of polycarbonate, the elastomer of the seal may be Santoprene®.

In this example, the blind central bore is of frustoconical shape with an angle of about 7°.

The inlet diameter, that is to say the upstream of the receptacle of the bore, is equal to the diameter of the reservoir.

The edges of the bore: intersection of the upstream face of the receptacle and frustoconical part of the bore do not intersect to form a sharp edge but these faces are connected with a suitable curvature that can be seen in FIG. 4.

Likewise, the edges of the radial channel: intersection of the radial channel and of the bore is rounded, with a smaller radius of curvature than in the previous case.

FIGS. 5, 6 and 7, which are partial perspective schematic views, show various embodiments of the arrangement of the inlet to an injection duct of a receptacle according to the invention. In these figures, the parts which are analogous are denoted by the same references as were used in FIGS. 3 and 4.

FIG. 5 shows a first embodiment of an inlet 39 with a spot face 59 centered on the injection duct 38 and a radial channel of constant width connecting the spot face and the central bore. In this example, the sides of the spot face and of the channel are perpendicular to the upstream face of the receptacle and to the closed end 19 of the inlet 39.

FIG. 6 shows another embodiment which differs from the previous one through the channel which is wider at the bore and converges somewhat to meet the spot face 59 centered on the injection duct 38.

FIG. 7 shows an embodiment with a channel of constant width, but the sides of the channel and of the spot face 59 are not perpendicular but are rounded to meet the closed end region 19 of the channel and of the spot face with a large radius of curvature; this is an inlet device of profiled section.

In these three diagrams, for the sake of simplicity, the intersections, on the one hand, between the bore and the upstream face of the receptacle and, on the other hand, the bore and the radial channels are depicted by arcs of a curve which give the impression of sharp edges; in point of fact, these sharp edges are blunted by sufficient curvature for the connections.

The invention claimed is:

1. A needleless syringe, comprising:
    a body having a downstream end;
    a cylindrical reservoir having opposite ends and housed by the body;
    a movable upstream stopper; and
    a movable downstream stopper closing the opposite ends of the cylindrical reservoir and entrapping an active principle, the movable downstream stopper comprising:
    a receptacle disposed at the downstream end of the body, the receptacle having an upstream face and at least two peripheral injection ducts each having inlets, said receptacle bearing via its upstream face against the reservoir, the receptacle further having a blind central bore;
    a driving means for moving the upstream stopper, the downstream stopper, and the active principle,
    wherein a free height of the blind central bore allows the inlets to the peripheral ducts to be uncovered when the downstream stopper is brought into contact with a closed end of the bore of said receptacle through the operation of the driving means, and wherein, on the upstream face of the receptacle, each inlet comprises a spot face positioned on the respective injection duct and is connected to a radial channel opening into the blind central bore, and the upstream face of the receptacle comprising a multilobed seal substantially parallel to the edge of the bore and substantially surrounding the inlets to the injection ducts.

2. The needleless syringe as claimed in claim 1, wherein said multilobed seal is housed in a groove of mating shape.

3. The needleless syringe as claimed in claim 1, wherein the upstream face of the receptacle comprises a two-shot injection molded multilobed seal substantially parallel to the edge of the blind central bore and surrounding the inlets to the injection ducts as closely as possible.

4. The needleless syringe as claimed in claim 1, wherein the spot face centered on the injection duct has a diameter ranging between about 1.1 times and 1.5 times the diameter of the injection duct and a depth ranging between about 0.5 times and about 0.6 times the diameter of the injection duct.

5. The needleless syringe as claimed in claim 4, wherein the radial channel has a constant width equal to the diameter of the spot face.

6. The needleless syringe as claimed in claim 4, wherein the radial channel has a width that increases from its point of connection to the spot face to its opening into the blind central bore where its width is at most equal to 1.4 times the diameter of the spot face.

7. The needleless syringe as claimed in claim 4, wherein the spot face and the radial channel are "profiled".

8. The needleless syringe as claimed in claim 1, wherein the blind central bore is of essentially frustoconical shape, the inlet diameter of the bore being equal to the inside diameter of the reservoir, the smallest diameter being toward the closed end of the bore and a running generatrix of the frustoconical lateral part making an angle of between about 2° and about 9° with the axis of the bore.

9. The needleless syringe as claimed in claim 8, wherein the upstream edges of the blind central bore and of the inlets have curvatures so as not to tear the downstream stopper.

10. The needleless syringe as claimed in claim 2, wherein the spot face centered on the injection duct has a diameter ranging between about 1.1 times and 1.5 times the diameter of the injection duct and a depth ranging between about 0.5 times and about 0.6 times the diameter of the injection duct.

11. The needleless syringe as claimed in claim 3, wherein the spot face centered on the injection duct has a diameter ranging between about 1.1 times and 1.5 times the diameter of the injection duct and a depth ranging between about 0.5 times and about 0.6 times the diameter of the injection duct.

12. The needleless syringe as claimed in claim 5, wherein the spot face and the radial channel are "profiled".

13. The needleless syringe as claimed in claim 6, wherein the spot face and the radial channel are "profiled".

14. The needleless syringe as claimed in claim 2, wherein the blind central bore is of essentially frustoconical shape, the inlet diameter of the bore being equal to the inside diameter of the reservoir, the smallest diameter being toward the closed end of the bore and a running generatrix of the frustoconical lateral part making an angle of between about 2° and about 9° with the axis of the bore.

15. The needleless syringe as claimed in claim 3, wherein the blind central bore is of essentially frustoconical shape, the inlet diameter of the bore being equal to the inside diameter of the reservoir, the smallest diameter being toward the closed end of the bore and a running generatrix of the frustoconical lateral part making an angle of between about 2° and about 9° with the axis of the bore.

16. The needleless syringe as claimed in claim 4, wherein the blind central bore is of essentially frustoconical shape, the inlet diameter of the bore being equal to the inside diameter of the reservoir, the smallest diameter being toward the closed end of the bore and a running generatrix of the frustoconical lateral part making an angle of between about 2° and about 9° with the axis of the bore.

17. The needleless syringe as claimed in claim 5, wherein the blind central bore is of essentially fi-ustoconical shape, the inlet diameter of the bore being equal to the inside diameter of the reservoir, the smallest diameter being toward the closed end of the bore and a running generatrix of the frustoconical lateral part making an angle of between about 2° and about 9° with the axis of the bore.

18. The needleless syringe as claimed in claim 6, wherein the blind central bore is of essentially frustoconical shape, the inlet diameter of the bore being equal to the inside diameter of the reservoir, the smallest diameter being toward the closed end of the bore and a running generatrix of the frustoconical lateral part making an angle of between about 2° and about 9° with the axis of the bore.

19. The needleless syringe as claimed in claim 7, wherein the blind central bore is of essentially frustoconical shape, the inlet diameter of the bore being equal to the inside diameter of the reservoir, the smallest diameter being toward the closed end of the bore and a running generatrix of the frustoconical lateral part making an angle of between about 2° and about 9° with the axis of the bore.

* * * * *